United States Patent [19]

Bepko et al.

[11] Patent Number: 5,491,095
[45] Date of Patent: Feb. 13, 1996

[54] SYSTEM AND METHOD FOR AGGULUTINATION DETECTION

[75] Inventors: Stephen Bepko, Catonsville; Donald M. McIver, Laurel; Francis J. Kaisler, Ellicott City, all of Md.

[73] Assignee: Westinghouse Electric Corp., Pittsburgh, Pa.

[21] Appl. No.: 67,278

[22] Filed: May 26, 1993

[51] Int. Cl.⁶ .................. G01N 33/546; G01N 33/557; G01N 33/94
[52] U.S. Cl. .................. 436/518; 436/533; 436/165; 436/807; 436/816; 436/901; 436/517; 435/7.1; 422/58; 422/63; 422/73
[58] Field of Search ............... 436/517, 514, 436/518; 435/7.1; 422/58, 61, 63, 68.1, 73, 82.05, 82.09

[56] References Cited

U.S. PATENT DOCUMENTS

| | | | |
|---|---|---|---|
| 4,398,894 | 8/1983 | Yamamoto | 436/517 |
| 4,597,944 | 7/1986 | Cottingham | 422/73 |
| 4,673,657 | 6/1987 | Christian | 436/501 |
| 4,806,015 | 2/1989 | Cottingham | 356/335 |
| 4,963,498 | 10/1990 | Hillman | 436/69 |
| 5,039,617 | 8/1991 | McDonald et al. | 436/69 |
| 5,178,836 | 1/1993 | Kitamori et al. | 422/73 |

*Primary Examiner*—Toni R. Scheiner
*Assistant Examiner*—Nancy J. Parsons

[57] ABSTRACT

A system and method of determining absence or presence of an illicit substance in a flowing mixture of requisite reagents by agglutination or lack thereof. A plurality of photodetectors are positioned over an illuminated read area oblique to a path of the flowing mixture. Signal samples of each of the detectors are processed individually. Successive samples are processed over a period time to detect differences or edges between relatively clear liquid and relatively opaque clusters in the flowing mixture. The illicit substance is determined in accordance with the number of variations in signal samples for a predetermined number of detectors.

6 Claims, 11 Drawing Sheets

1 NEGATIVE INPUT

3 NEGATIVE HIGH PASS FILTER

SYSTEM AND METHOD FOR AGGULUTINATION DETECTION

BACKGROUND OF THE INVENTION

1. Field of the Invention

The present invention relates to the detection of chemical substances; and more particularly to method and system for determining the presence or absence of a target sample in an antibody/antigen mixture.

While the invention is subject to a wide range of applications it is especially suited for use in a system and method for rapidly determining whether a target substance is heroin, cocaine, or other illicit chemical; and will be particularly described in that connection.

2. Description of Related Art

In enforcing the prohibition against the possession of illicit substances, it is important that an accurate determination of a substance suspected of being illicit is made rapidly.

Without being able to obtain a rapid objective determination as to whether or not substances that are suspected of being or containing an illicit substance, customs agents, airport officials, or other drug enforcement officers either detain and embarrass innocent persons needlessly, or permit violators to evade being apprehended for fear of such wrongful detainment.

A well-known technique for detecting the presence of a wide variety of chemical substances uses antibody/antigen reactions. With this technique, microscopic particles, to which the antibody or antibody generator are chemically attached, are made to agglutinate or are inhibited from agglutinating in the presence of a particular target sample.

One type of agglutination reaction that is used for detecting the presence or absence of cocaine or heroin, for example, is known as latex agglutination. When the antibody and the target substance are first mixed, the result is a uniform milky substance. If cocaine or heroin is not present in the mixture, the antibodies and latex particles interact and combine. After a period of time many linkages are formed, which manifest themselves as visible clusters in the substances thus causing the mixture to lose its uniform milky texture. However, if cocaine or heroin is present in the mixture, the particles and the antibody generator do not combine and the uniform milky characteristic persists. The reaction of the mixture which results in the clusters and destruction of the uniform milky quality of the mixture is referred to as a negative result and the persistence of the milky characteristic, which is caused by the presence of heroin or cocaine, is referred to as a positive result.

As far as is known, prior art systems typically used for carrying out this procedure require several steps, which are not conducive to being used in the field. Also, the necessity of measuring the reagents in the exact proportions, and the necessity of maintaining a particular orientation during the flow of the mixed fluid, as well as requiring human judgement in determining the result, all contributed to the difficulty in carrying out the procedure involving antibody/antigen reactions.

In light of the foregoing, there is a need for a method and system for detecting illicit substances, which does not involve subjective human judgment, and which provides a definitive reliable response in a short period of time.

SUMMARY OF THE INVENTION

Accordingly, the present invention is directed to a method and system that substantially obviates one or more of the problems due to limitations and disadvantages of the prior art.

Additional features and advantages of the invention will be set forth in the description which follows, and in part will be apparent from the description, or may be learned by practice of the invention. The objectives and other advantages of the invention will be realized and attained by the system and method particularly pointed out in the written description and the appended drawings.

To achieve these and other advantages, and in accordance with the purpose of the invention, as embodied and broadly described, the invention is a system for determining the presence or absence of a target substance in a mixture including requisite reagents that include a device for storing reagents, introducing the target substance, and when activated mixing the reagents and target substance, flowing the mixture along a path past a transparent read area; a source of illumination positioned adjacent the read area for illuminating the flowing mixture; a plurality of detectors positioned at the read area for detecting light in respective portions of the read area in accordance with the translucence of the flowing mixture, each of said detectors generating an output signal having an amplitude that corresponds to the amount of light received from the respective portion of the read area; means for calculating the amplitude variations of the output signal of each detector; means for determining the amount of variation that exceeds a selected threshold value; and means for displaying in the alternative the presence or absence of the target substance in accordance with the total amount of variation for each of a predetermined number of the plurality of detectors.

In another aspect, the invention is a method of determining the presence or absence of a target substance that includes the steps of mixing a target substance with requisite reagents, flowing the mixture past an illuminated read area, detecting variations in the illumination at a plurality of portions of the read area, said variations corresponding to respective variations in translucence in the respective portions of the read area, determining the presence or absence of the target substance in accordance with the amount of variations exceeding a predetermined threshold in a predetermined number of sections of the read area, and indicating in the alternative the determined presence or absence of the target substance.

It is to be understood that both the foregoing general description and the following detailed description are exemplary and explanatory and are intended to provide further explanation of the invention as claimed.

The accompanying drawings are included to provide a further understanding of the invention and are incorporated in and constitute a part of this specification, illustrate one embodiment of the invention, and together with the description serve to explain the principles of the invention.

DETAILED DESCRIPTION

Figure 1:
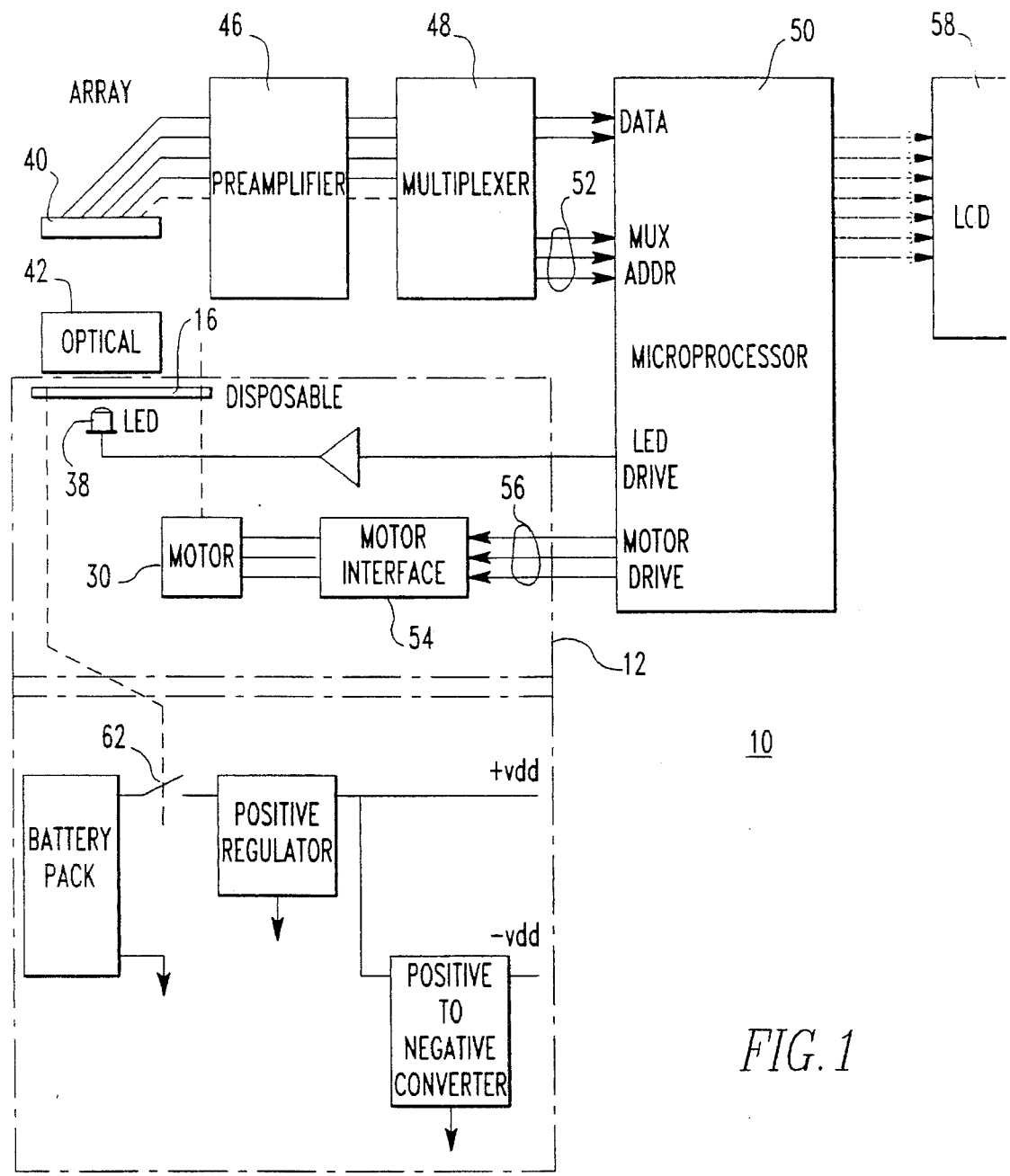
FIG. 1 is a block diagram of a system in accordance with one embodiment of the present invention.

A system for determining the presence or absence of a target substance in a mixture including requisite reagents is exemplified and generally referred to as 10 in FIG. 1. The system includes a device for storing reagents, introducing the target substance, and when activated mixing the reagents and target substance, and flowing the mixture along a path past a transparent read area.

Figure 2:
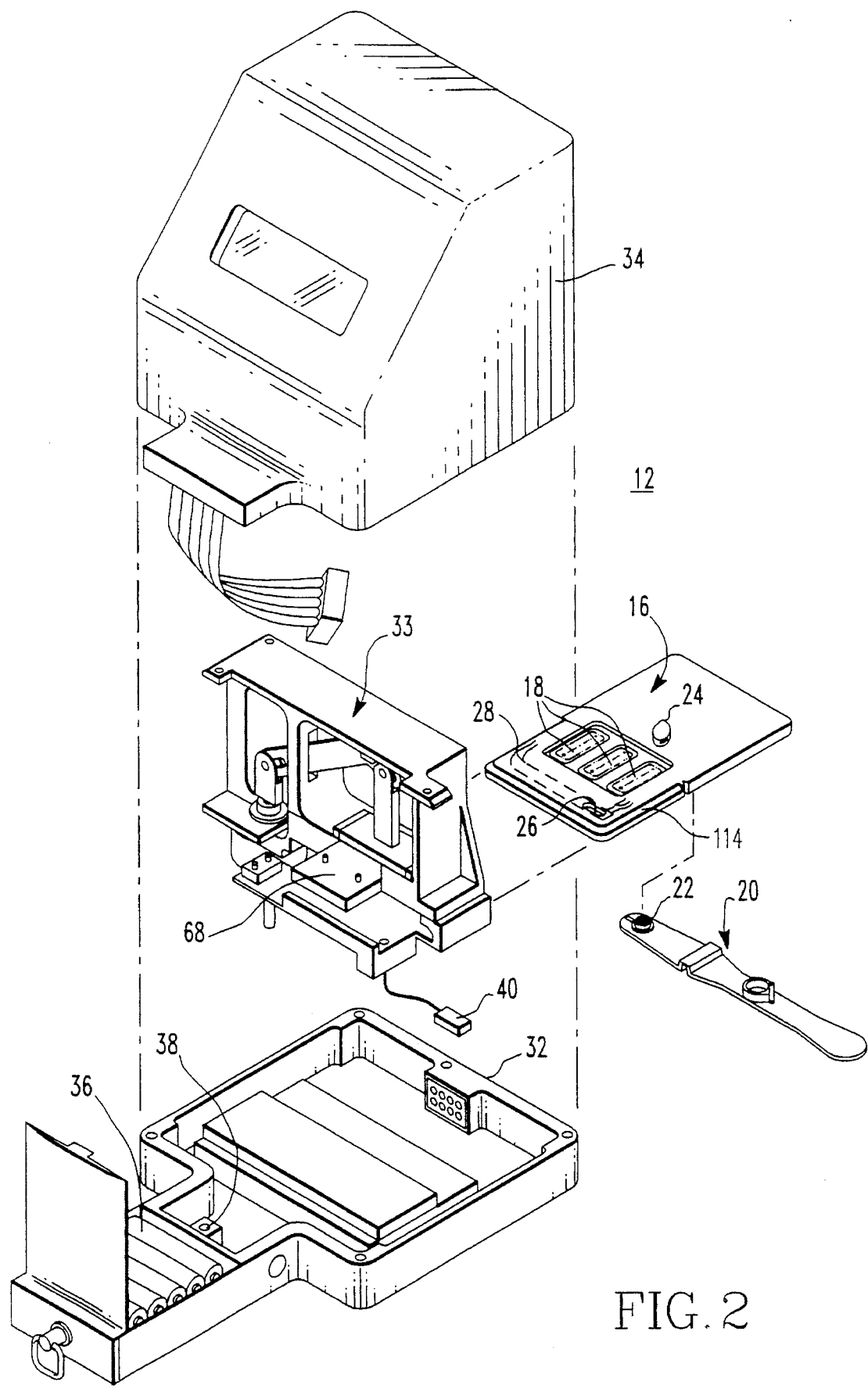
FIG. 2 is an exploded view of one embodiment of an apparatus that may be used in implementing the system of FIG. 1.

As herein embodied, such a device is schematically shown in FIG. 1 within the dashed lines 12; and a specific example of the device 12 is referred in FIG. 2.

The device 12 may be any one of a plurality of proposed devices that stores the required reagents, introduces the target substance, and is activated to mix the reagents and target substance and flow the mixture along a path past the transparent read area. Preferably, such a device is one that is similar to that described in a U.S. patent application filed on Dec. 8, 1992 and an titled DISPOSABLE OPTICAL AGGLUTINATION ASSAY AND METHOD FOR USE bearing Ser. No. 986,816 and assigned to the same assignee as the instant application. The aforementioned U.S. patent application is incorporated by reference for a more detailed description.

Referring to FIG. 2, device 12 preferably includes a disposable card 16 with a plurality of bladders or storage reservoirs 18 for storing reagents and releasing the reagents in response to lateral pressure. The number of bladders or storage reservoirs 18 is dependent upon the reagents that are required for detecting a particular target substance. A swab 20 which may be removably attached to the card 16 is used for introducing the target substance into the mixture. Swab 20 has a gathering surface 22 for collecting sample particles of the target substance as it is brushed across a suspected surface. Swab 20 when placed in a position relative to the card 16 so that the collecting surface 22 covers an entry port 24, any particles on the collecting surface 22 are released into a mixture of the reagents as is described in more detail in the incorporated U.S. patent application Ser. No. 986,816 filed on Dec. 8, 1992. The card 16 also include a read area 26 aligned with a path 28 through which the mixed fluid flows after leaving entry port 24. The flowing of the reagents and the target substance is accomplished by a mechanical apparatus referred to at 33. The device 33 includes a stepping motor 30 (See FIG. 1) that incrementally squeezes card 16 for causing the reagents and the target substance to mix and flow through the various paths into a reservoir formed in the card 16. The motor device 28 is mounted to a base 32 over which a housing 34 fits to complete the unitary device 12. Power for the device 12 is provided by batteries 36. Disposable card 16 slidably fits beneath the member 68 so that the read area 26 is aligned with an LED 38 to provide illumination to the read area 26 from beneath the card 16.

In accordance with the invention, a plurality of detectors are positioned at the read area for detecting light in a plurality of portions of the read area in accordance with the translucence of the flowing mixture. Each of said detectors generating an output signal having an amplitude that corresponds to the amount of light received from a respective portion of the read area.

Figure 3:
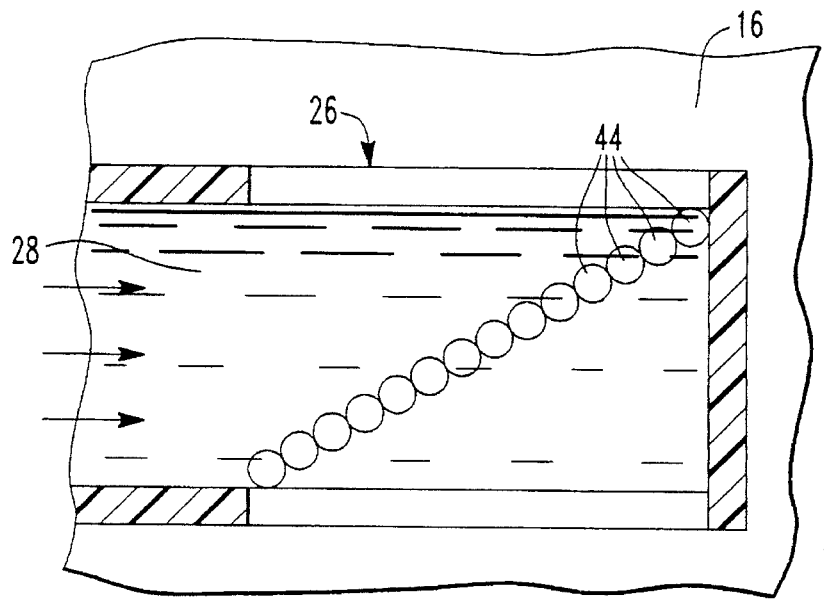
FIG. 3 is a highly magnified diagram of a read area together with a preferred arrangement of the photodetectors in the system of the present invention.

Referring again to FIG. 1, and as herein embodied, an array of detectors referred to generally as 40, is positioned above a lens system 42 which projects an image of the chemical stream mixture onto the array of detectors. As shown in more detail in FIG. 3, the read area 26 exposes a section of the path 28 along which the mixture flows during operation of the system. Spaced above the read area 26 and aligned at an oblique angle in the direction of flow of the mixture along a path 28 are a plurality of individual photodetectors 44. Each of the detectors senses the amount of transmitted light of that portion of the liquid flowing directly beneath it in the path 28. Thus, the flowing liquid is monitored from one side of the path to the other in the direction of flow of the liquid. The arrangement of the detectors shown in FIG. 3 is preferred in that a greater number of individual detectors, such as fourteen in the described embodiment, can be effectively utilized. However, the detectors 44 could be arranged transversely across the path 28 in a direction perpendicular to the flow of fluid, for certain applications. Of importance however, is that each of the detectors detect the fluid in a section of the path extending from one side to the other. This is important because of streaking and bubble formation in the fluid path.

Each individual detector 44 of the array 40 generates an output signal having an amplitude that corresponds to the amount of light received from a respective lateral portion (small area) of the path at the read area. The output of each detector 44 is processed separately.

As shown in FIG. 1, the array of detectors 40 is connected to a preamplifier 46 for amplifying the signal output from a respective detector 44. The preamplifier 46 is connected through a multiplexer 48 to an A/D converter (not shown) of a microprocessor 50. The microprocessor 50 receives the amplified data from each detector 44 of the array 40 in a sequence that is controlled by multiplexer 48 which receives the respective detector addresses over lines 52. The LED 38, which illuminates the read area 26 is controlled by a drive circuit of the microprocessor 50. Stepper motor 30, which is coupled to the microprocessor 50 via a motor interface 54 is operated by the microprocessor 50 over lines 56 as hereinafter described. The system 10 includes a display 58 which is connected to the output of the microprocessor 50 for indicating the results of the tests. As herein embodied, the display is preferably a liquid crystal display 58.

A switch 62 is provided to activate the device upon the insertion of the card 16 to the proper position where the read area of the card is aligned with the LED and the detectors 44. The lens system 42 provides imaged light from the read area to the detector elements 44.

Figure 4A:
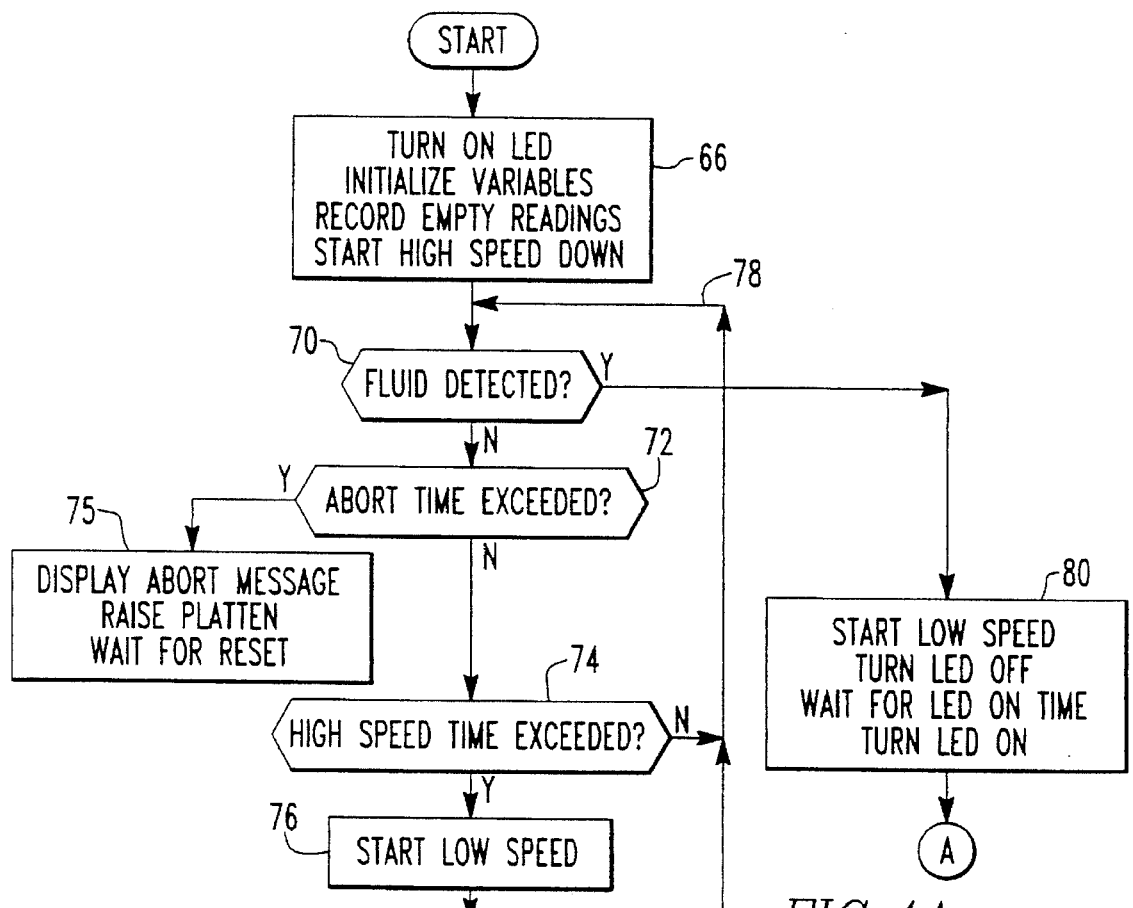
FIGS. 4A, 4B, and 4C are flowcharts illustrating the image processing of the read area according to one embodiment of the invention.

In accordance with the invention, means are provided for calculating variations in the output of each of the plurality of detectors. As herein embodied and referring to FIGS. 4A, 4B, and 4C, the microprocessor 50 first initialized variables; and the signal values of each of the detectors 44 is stored prior to any mixing by the fluid as indicated in step 66 of FIG. 4A. In the same step, the step motor 30 is energized which operates a platten 68 to press downwardly and squeeze the bladders 18 to force the reagents out of the bladder to mix with the substance at port 24. The motor 30 is initially operated at high speed to provide rapid discharge and mixing from the storage reservoirs or bladders 18 as indicated at step 66. As indicated, if FIG. 4A, during high speed operation, the system continuously and alternately checks for three events: fluid detection at step 70, Abort Timeout at step 72 and High Speed Timeout at step 74. When fluid is detected, the system stops checking for Abort Timeout at 72 and High Speed Timeout at 74, and stops high speed operation and proceeds with normal low speed operation at step 80. If Abort Timeout at step 72 is exceeded without fluid detection, the system displays an abort message, raises the platten and stops at step 74. If the High Speed Timeout at 74 limit is exceeded, the system starts low speed at step 76 but continues to look for fluid at 78. Normally the system will detect fluid before either of the time out limits is exceeded. The Abort Timeout is used to quickly reject a defective card; i.e., if the card has a leak or not enough reagents. The High Speed Timeout avoids bottoming the platten during high speed down, if the fluid is just moving too slow for some reason, for example, low temperature. The fluid continues to move quickly for some distance after switching from high to low speed. If it is detected before Abort Timeout at 72, normal system operation resumes as indicated at step 80. Otherwise the system will abort at step 75.

Once fluid is detected, the LED is turned off as shown at step 80 to save battery energy during the period of time required for the reaction to become observable. At the expiration of approximately twenty three seconds of low speed operation, according to one embodiment of the invention, the LED is turned on. At this point the test commences and sample detector readings are taken at regular intervals as indicated in step 82 in FIG. 4B. In one embodiment of the invention, the samples are taken in one quarter second intervals.

At each sample interval, the status of each channel is determined as follows. A counter, herein referred to as the Negative Count, is set to zero as indicated at step 82. In step 86, the channel is checked for obscuration. A channel could be obscured if the card was inserted improperly and the detector is not receiving enough light. This is determined by comparing the detector value before fluid was detected, which was determined in step 66, with a constant threshold. If the value is too low, then the channel is obscured and that channel in not analyzed further. If the channel is not obscured, then the low pass value, the high pass value and the high pass threshold are determined as indicated in step 88. According to one embodiment of the invention, the filter threshold equations are;

$$LP_i = K1*Input_i + (1-K1)*LP_i - 1$$

$$HP_i = HP_i - 1 + Input_i - LP_i$$

$$Threshold_i = minimum\ (i*Empty*K2*sqr*(LP_i),\ 10)$$

In these equations, $LP_i$ is the current low pass value, $K1$ is a constant equal to 0.73, $Input_i$ is the current channel reading, $LP_{i-1}$ is the previous low pass value, $HP_i$ is the current high pass value, $HP_{i-1}$ is the previous high pass value, threshold $_i$ is the current high pass threshold value, i is the number of samples taken since the test commenced, Empty is the channel reading before any fluid was detected in the read area, $K2$ is a constant equal to 0.000021, and sqr $(LP_i)$ is the square of the current low pass value. The minimum function limits the high pass threshold to be not less than 10.

If the high pass value exceeds the high pass threshold, as indicated in step 90, the negative count is increased by one, indicated in step 92; otherwise the negative count is not incremented. The next channel is processed, indicated in step 94.

After all channels have been processed for one sample, if the number of channels that exceeded the high pass threshold exceeds a predetermined value, indicated in step 98, the card is deemed to be negative, i.e., the sample does not contain the illicit substance, and testing terminates immediately. Otherwise, if a time limit, in one embodiment, 60 seconds, is not exceeded, testing resumes with the next sample, indicated by 96. When testing terminates either by the negative determination, at step 98, or time limit exceeded at step 96, processing resumes with step 102. If testing terminated due to the time out limit being exceeded, then a positive result is indicated and the illicit substance is present.

There are two factors that may distort the analysis of a sample, one of which is bubbles and another of which is streaking. Bubbles may be formed during the initial stages when the fluid is pushed fast to produce adequate mixing; and large bubbles get lodged at random spots along the path of the flowing liquid. During the second fluid motion phase, that is, where the stepper motor 30 is operated at a slow rate (see step 80) the fluid flows around the bubbles. Small bubbles on the other hand will move with the fluid and not get lodged. If a large bubble lodges under the read area 28 in the field of view of one or more of the detectors 44, those detectors will see a large signal level with little variation, which would cause an otherwise negative sample to appear positive. A small bubble moving through the read area produces a variation which could cause a positive sample to appear negative. It has been shown that small bubbles are not of great concern because they occur very infrequently during the sampling time, i.e., they usually pass by the read area in the first thirty seconds; and small bubbles do not produce enough variation to exceed the high pass threshold because of their low density. Large bubbles, on the other hand, can completely block one or more of the detectors with the fluid flow being deflected into the field of view of adjacent detectors. If a very large bubble blocks many detectors then those detector elements see a high value transmission and a low intensity variation, i.e., that is, bubbles are usually clear. In actual practice, as many as nine of the fourteen detectors 44 in the described embodiment have been simultaneously blocked by a large bubble. Since a positive indication and bubbles both produce low variation, it is important to detect and invalidate tests where the low variation is due to bubbles. This is accomplished as indicated in FIG. 4C hereinafter described.

Streaking is caused by poor mixing of the reagents during high speed operation and is most evident on positive tests. The fluid mixture appears in bands of alternating clarity. If the bands move back and forth across the read area 28, as they sometimes do, it causes a variation in the detector signals, which tends to look negative. Since this variation occurs more slowly than variation due to agglutination, the low pass filter equation and the high pass filter equation are set so this variation does not cause the channel to be counted negative in step 100.

Figure 4B:
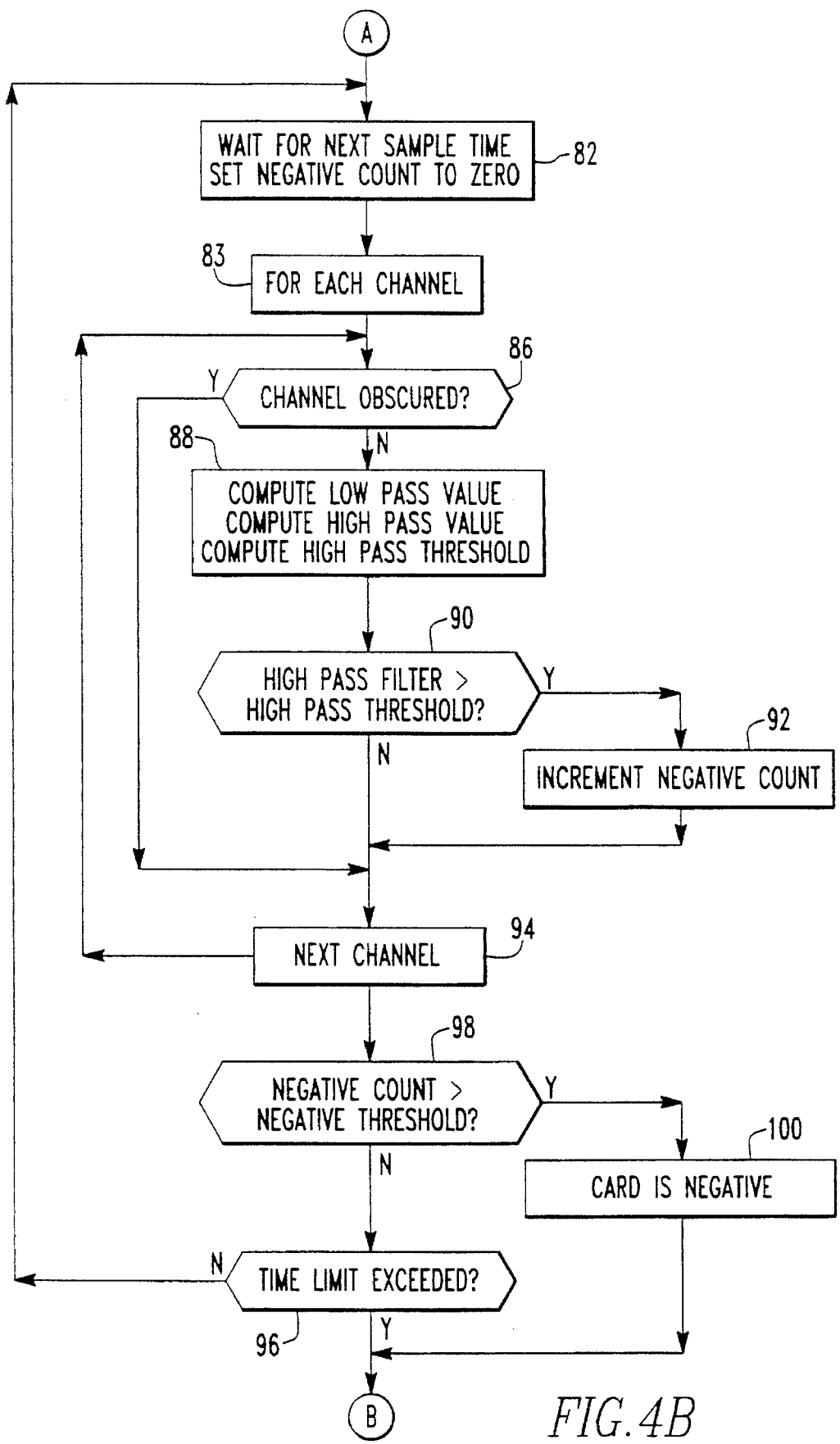
Figure 4C:
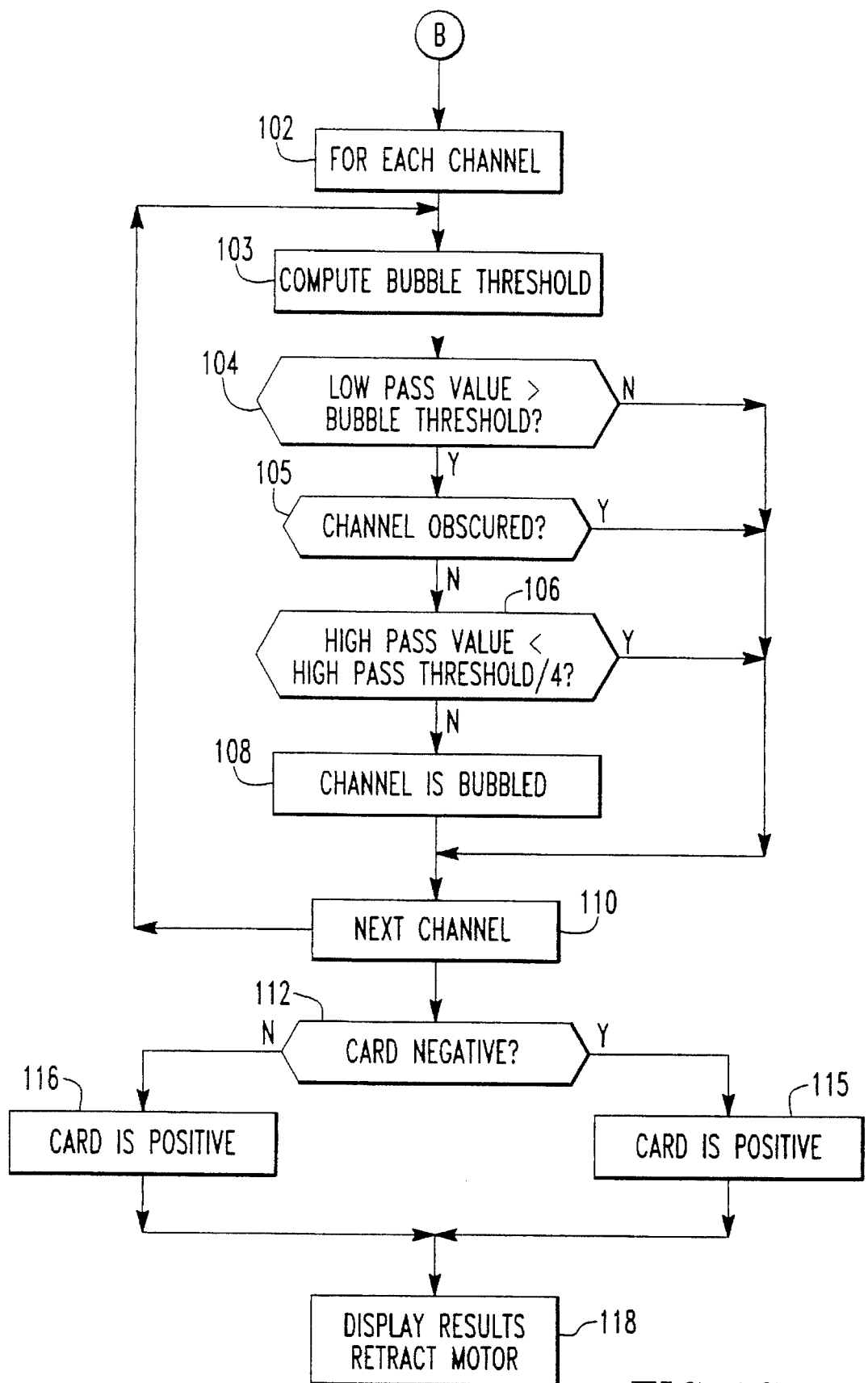

Referring to FIG. 4B and 4C, if a negative count for a particular channel has not exceeded a negative count threshold, and the time limit for running the test has expired as indicated at step 96, then for each such channel as indicated at 102, a bubble threshold is computed at step 103 of FIG. 4C which threshold corresponds to approximately 75 to 80 percent of the empty value of a respective detector that was initially stored prior to the flow of fluid past the read area. If the low pass filter value of a particular sample exceeds the bubble threshold at step 104, and the high pass filter value is less than one quarter of the high pass threshold at step 106 and the channel is not obscured, then this particular channel is determined to be bubbled as indicated at step 108. The next channel is then addressed at step 110. If the card has not yet been declared negative at step 112, and too many of the channels have been determined to be bubbled at step 114, then the card is declared invalid at step 115. However, if the card is not determined to be negative or invalid, then it is positive as indicated in step 116. In any case the results are displayed and the stepping motor is retracted at step 118, after which processing stops.

Figure 5A:
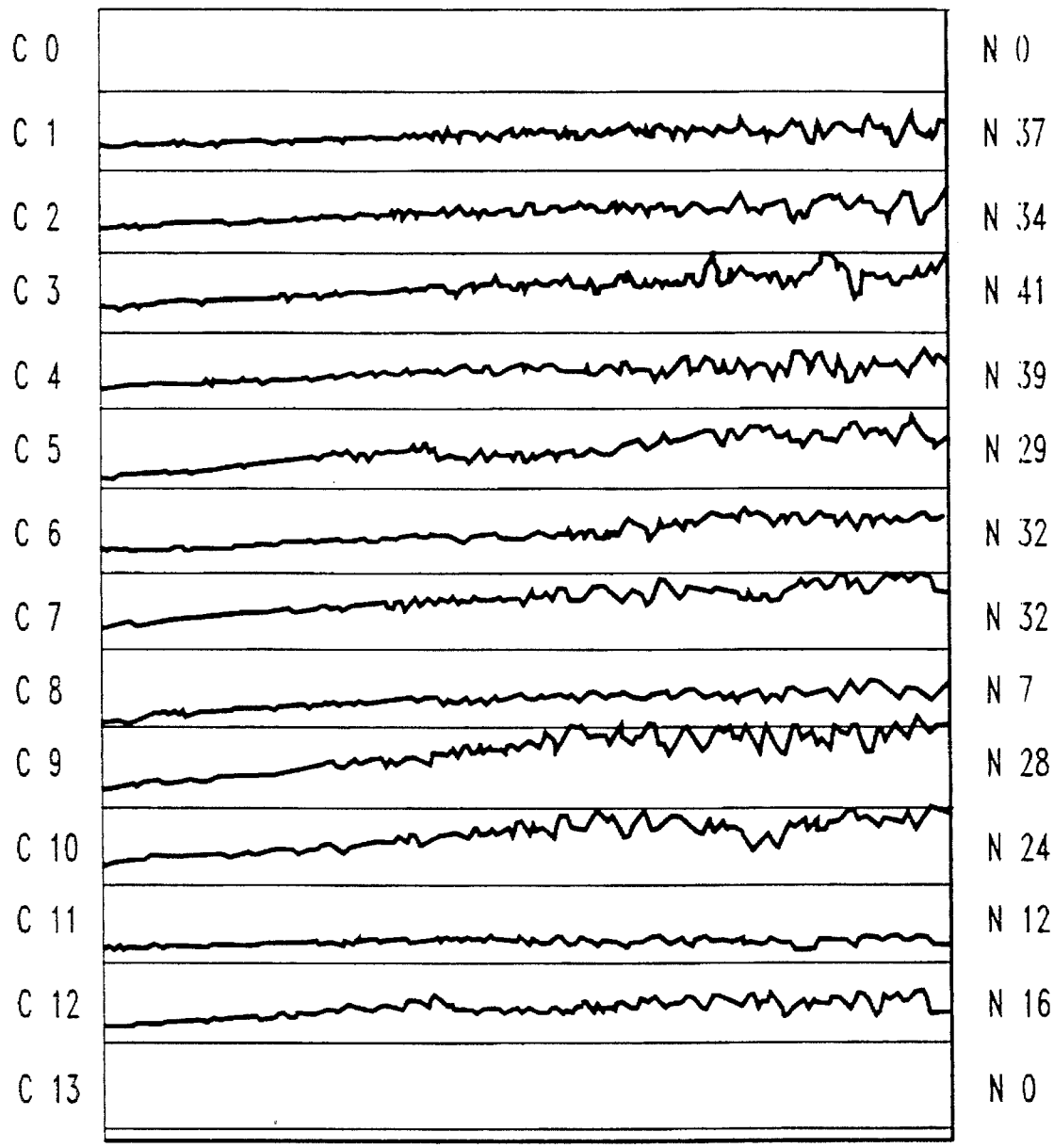
FIG. 5A is a graphical representation of the raw input of each of the detectors for a negative result.
Figure 5B:
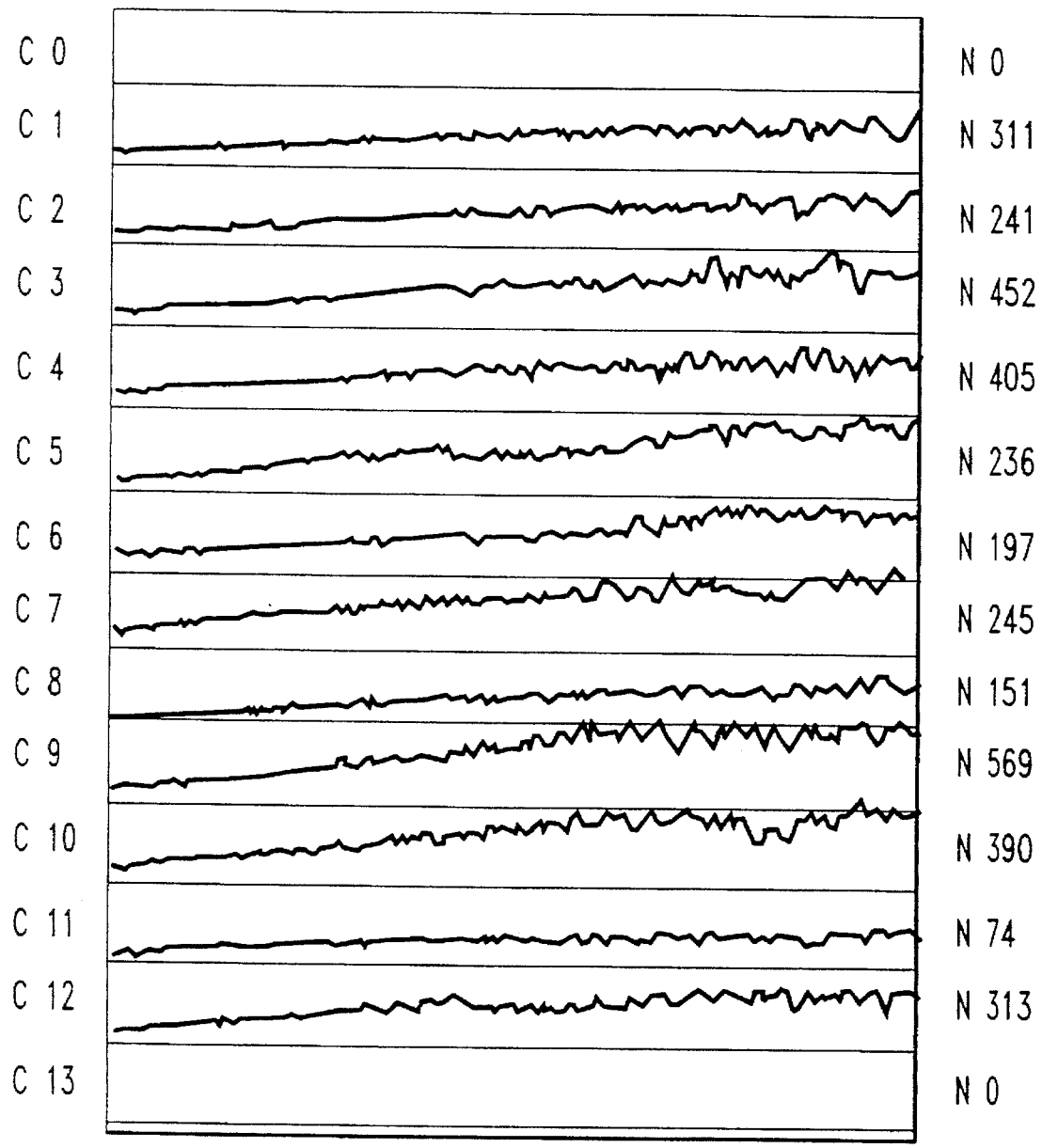
FIGS. 5B and 5C are graphical representations of the cumulative outputs of the low and high pass filters for a negative result.
Figure 5C:
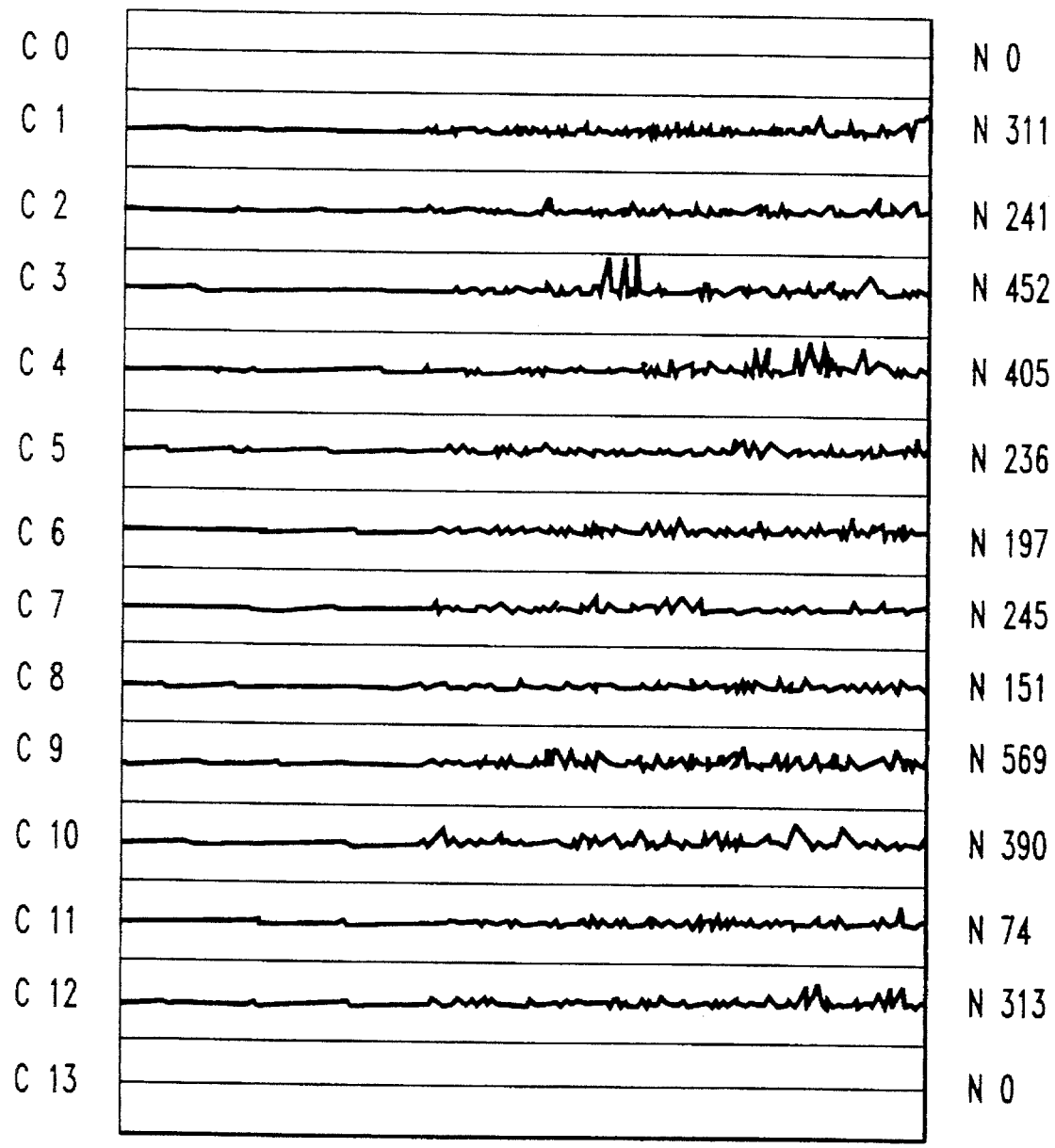
Figure 5D:
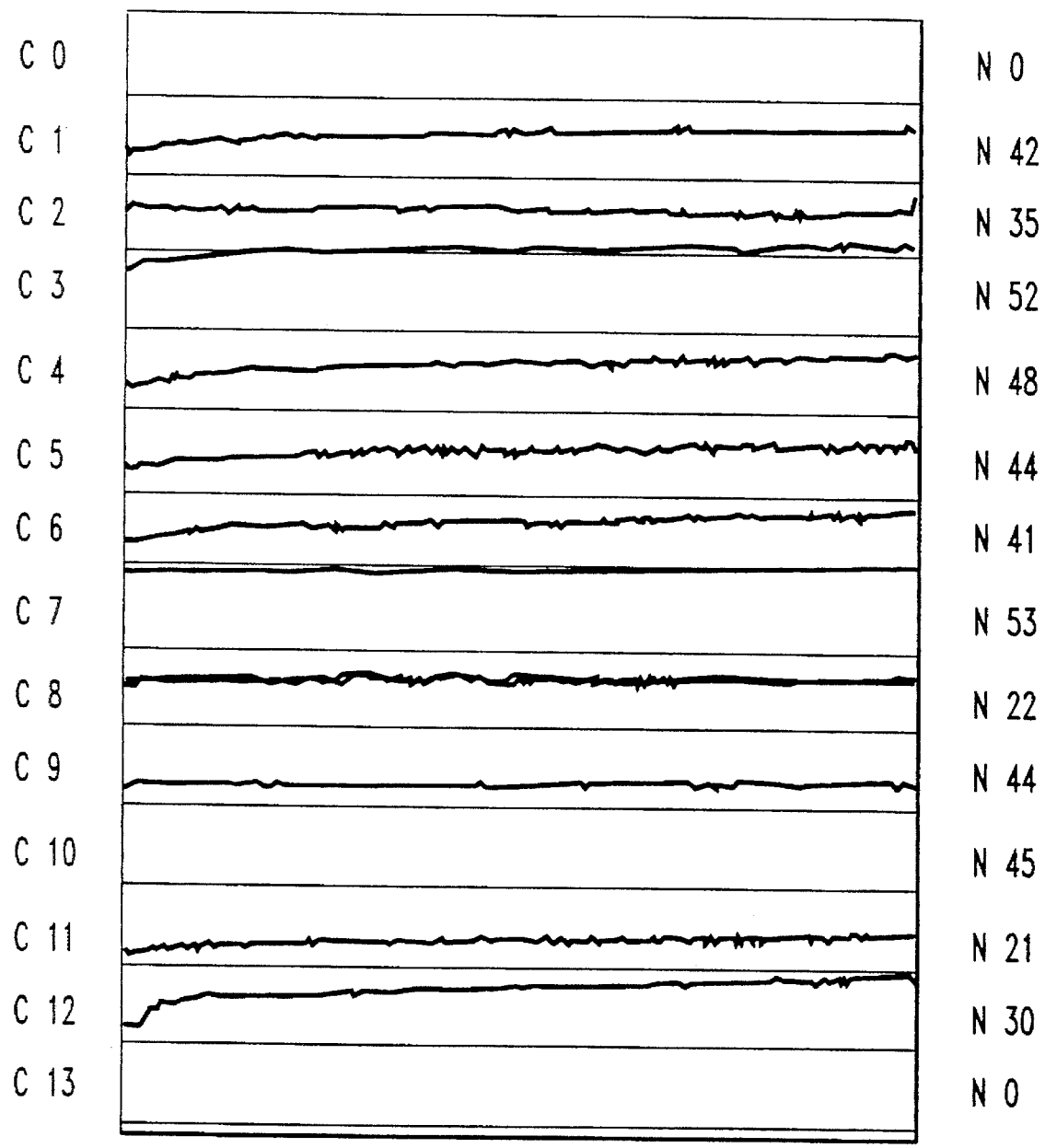
FIG. 5D is a graphical representation of the raw input of each of the detectors for a positive result.

A description of the present invention will now be given with reference to FIGS. 5A–5E in connection with the operation of the system 10. Initially, the gathering portion 22 of the swab 20 is dragged over an area or dipped in a container suspected of containing the target substance. The gathering portion 22 is then inserted in the inlet opening 24 of the disposable card 16. When the card is inserted to align with the reader 28 as previously described, it activates a switch 62 that activates the system on. After initialization, a motorized platten 68 presses on the bladders or storage reservoirs 18. The fluids in the reservoirs mix and flow across the inlet port 24, then along a path the read area and finally to an accumulation area in the card (not shown). The light emitting diode (LED) illuminates the underside of the card 16 at the read area 28. Lens assembly 42 images the mixture as it passes the read area onto the fixed linear detector array 40. Immediately after mixing, the fluid mixture has a smooth, milky consistency. If the specific substance which is being tested for is present on the swab, even in trace quantities, the texture of the fluid s surface does not change significantly. However, if the substance is not present, the mixture agglutinates; i.e., white particles form in the mixture and the remaining fluid looks clear. Thus, the particles in the moving stream in the read area cause an intensity modulation on the detector array elements and create an AC current component. Referring to the diagram of FIG. 5A, each one of the curves C0 through C13 represent the alternating current input to the microprocessor 50 of a corresponding one of the detectors 44 during a negative test. During the time period for carrying out the test, the number of times that the variation exceeded the calculated threshold is indicated by the numbers. The detectors C0 and C13 which are assumed to be obscured showed no output. Referring to FIG. 5D, the curves C0 through C13 represent the alternating current input to the microprocessor 50 during a positive test. Note that without the filtering as described the resulting number of variations is similar to the negative test of FIG. 5A. Note that curves of FIG. 5A and 5D are each on a scale of zero to one hundred.

The currents produced are converted into voltage signals at 46 multiplexed at 48, converted to digital signals in the microprocessor 50. The voltage signals of each of the detectors 44 are then sampled at an approximate 4 hertz rate by the microprocessor 50 to determine if agglutination (particle clumping) is occurring or not.

Figure 5E:
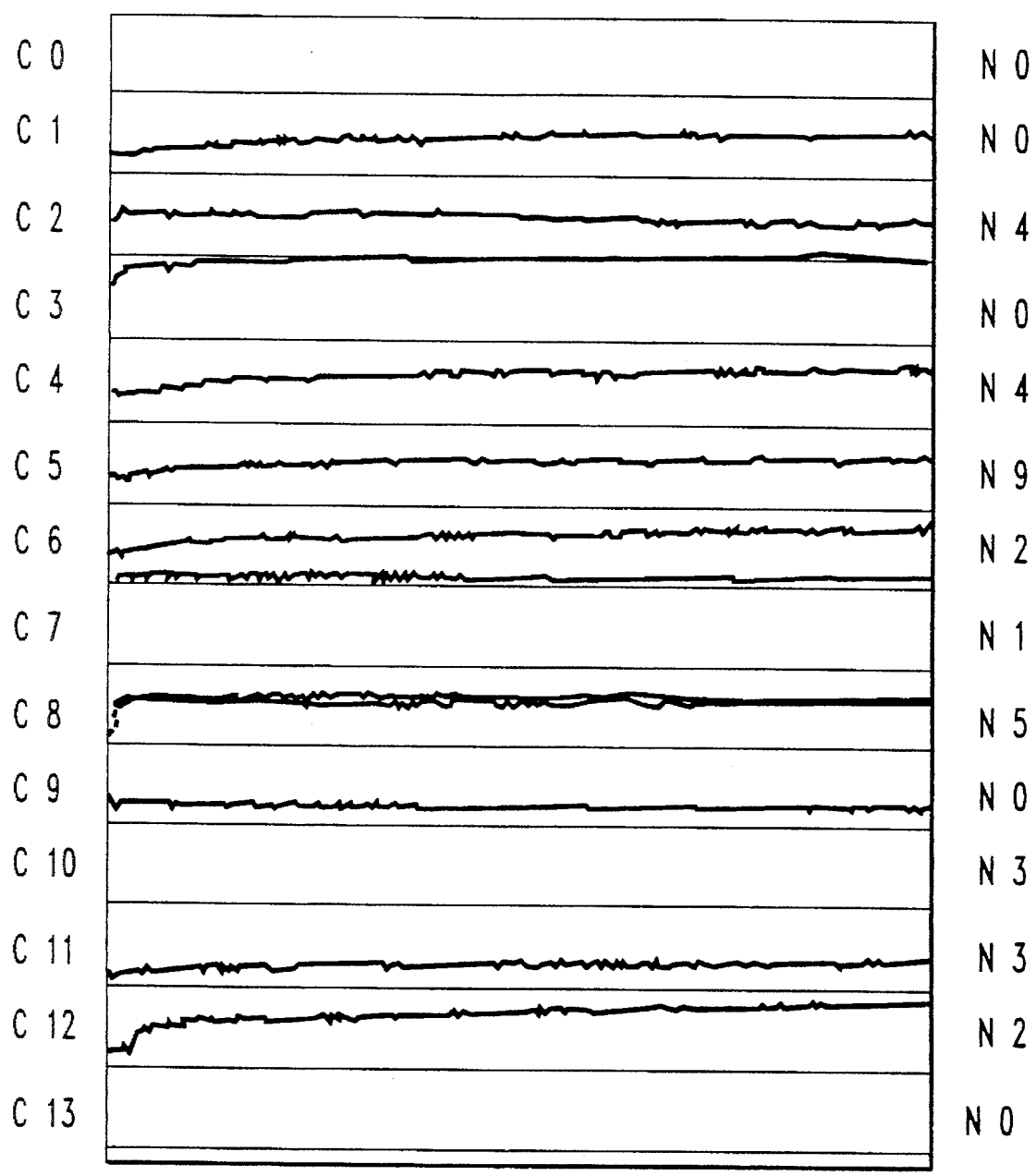
FIGS. 5E and 5F are graphical representations of the cumulative output of each of the low and high pass filters for a positive test.
Figure 5F:
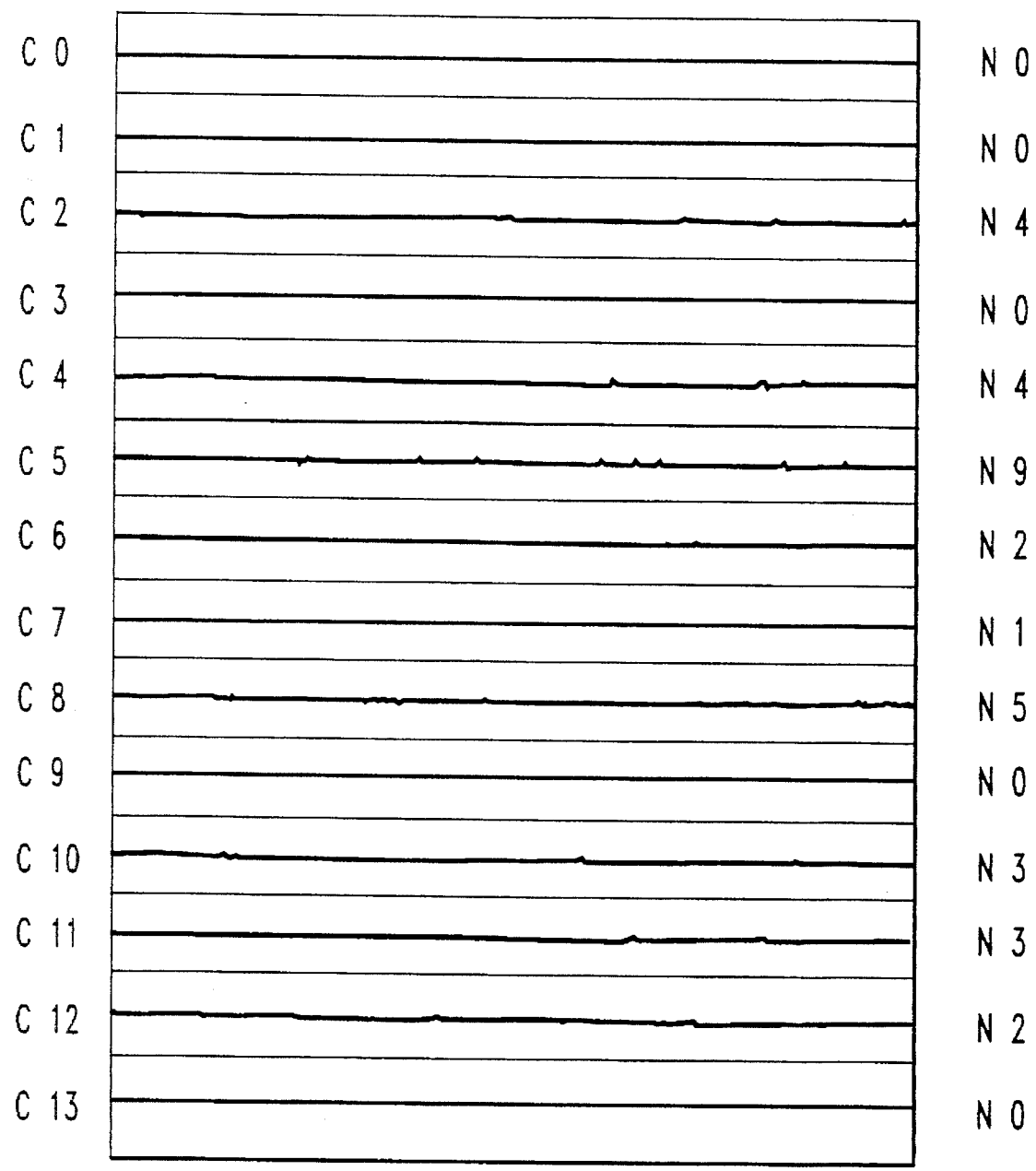

Since it takes the reaction approximately 10 to 30 seconds (depending on the chemistry being used) to produce suitably sized particles to which the detectors are sensitive, the outputs of the filters are ignored until a specific time interval after mixing. Once the data collection begins, the square of the high pass filter values are accumulated over time and compared against a threshold that increases with time. This threshold starts at an arbitrary value, for example, cocaine may have a threshold value of 10 and heroin a threshold value of 25. Cocaine would increment by an integer of 1 at each sample interval while heroin would increment by an integer 2 at each sample interval, for example. When a certain percentage of the plurality of detectors which in the present embodiment is 14, exceeds the thresholds simultaneously, a negative result is immediately enunciated on the liquid crystal display 58. Referring to FIG. 5B, curves C0 through C13 represent the cumulative output of the low pass filter equations during a negative test. The cumulative totals are on a scale of one to one hundred similar to FIG. 5A and FIG. 5D. Note that the number of variations, at the output of the low pass filter is substantiated. Referring to FIG. 5C, which shows a number of variations on the right hand side of the diagram, as being the same as FIG. 5B, is on a scale from −20 to +20. FIG. 5E and 5F are diagrams of the cumulative variation for a positive test at the output of the low pass filter and the high pas filter respectively. Although there are a few variations, the difference in number between the filtered positive and filtered negative is substantial, from single digit to triple digit totals. In contrast is the number of variations for a positive and negative card prior to being filtered. Note, that without the filtering, that the number of variations between a negative and positive test is minimal. It is preferable that the detection algorithm described in connection with FIGS. 4A, 4B and 4C err on the side of producing a negative result. Generally, if three channels go negative, more will follow soon. A positive result is indicated if the process proceeds for a specified period of time, for example, cocaine 50 seconds and heroin 25 seconds, with less than the required percentage of data channels exceeding the negative thresholds. As previously described, each detector or channel output is processed separately which reduces the need to equalize response between detector channels and avoids problems with uneven agglutination which normally occurs.

In the present embodiment, if a detector produces a low pass filter value higher than 0.75 to 0.80 times the empty value and the high pass filter value is less than 0.25 times the high pass threshold then the presence of a bubble is as assumed. The number of bubbles are computed at the end of a positive determination. In one application, the computed positive result is invalidated if four or more detectors are blocked. A negative determination is never invalidated due to bubbles in the embodiment described.

In summary, a method has been described for electronically determining the presence or absence of a target substance, such as trace chemicals using antibody/antigen reactions, such as latex agglutination/antibody chemistry for example. The technique images the surface of the chemical reaction region as the fluid flows by, the image is analyzed for "edges," indicating particulate formation. Trace substances such as cocaine or heroin will inhibit the reaction so that no edges occur. The image attributes are analyzed over a small time interval such as 20 to 50 seconds, and a decision is made based on the output of an algorithm applied to the collected data. Such a method is not subject to human error.

The method of the present invention also provides advantages in that the fluid moves faster in the center of the channel than on the edges when there are no bubbles present, which causes the center detectors to sense agglutination first. Frequently, the edge detectors never detect agglutination at all. However, on any given run, bubbles can reverse this entirely. Center detectors see nothing while the edges detect agglutination. The system and method of the present invention minimizes errors under such conditions.

It would be apparent to those skilled in the art that various modifications and variations can be made in the system and method of the present invention such as the specific number of detectors utilized, or the specific manner of calculating the variations, or the particular parameters being used, for example, without departing from the spirit or scope of the invention. Thus, it is intended that the present invention cover the modifications and variations of this invention provided they come within the scope of the appended claims and their equivalents.

What is claimed is:

1. A method of determining the presence or absence of a target substance in a sample comprising:

combining the sample with agglutination reagents specific for the target substance to form a reaction mixture;

flowing the reaction mixture along a path having a predetermined width past a transparent read area;

illuminating the flowing mixture at the read area;

detecting in a direction from one side of the path to the other at a plurality of read area locations light received through the flowing mixture;

generating a series of signals for each of the plurality of read area locations having a value corresponding to the detected illumination;

calculating variations in the value of the signals at each read area during a predetermined time interval, wherein the step of calculating the variations in the signals comprises the substeps of passing each signal of each detector through a low pass filter equation $$LP_i = K1 \text{ Input}_i + (1-K1)°LP_i-1$$

and a high pass filter equation $$HP_i = HP-1 + \text{Input}_i - LP_i,$$

where i is the current signal number, $\text{Input}_i$ is the current input signal, K1 is a filter constant between 0 and 1, $LP_i$ is the current accumulated Low Pass filtered data, and $HP_i$ is the current accumulated High Pass filtered data;

determining the absence of the target substance in the flowing mixture in response to the calculation of a predetermined number of calculated variations for each of a predetermined plurality of the read area locations; and determining the presence of the target substance in the flowing mixture in response to calculation of less than the predetermined number of value variations during the predetermined time interval.

2. The method of claim 1 wherein the step of detecting a plurality of read area locations comprises positioning a linear array of detectors obliquely relative to the path of the flowing mixture.

3. The method of claim 1 wherein the step of calculating the variations in the value of the signals includes the substeps of comparing each of the series of calculated variations with a threshold value; and counting each variation that exceeds the threshold value.

4. The method of claim 3 wherein the substep of comparing each of the calculated variations with a threshold value, includes calculating a new threshold value for successive calculated variations.

5. The method according to claim 4 wherein the substep of calculating a new threshold value comprises calculating the threshold in accordance with the equation $$\text{Threshold} = \text{minimum}(i°\text{Empty}°K2°(LPi)^2, 10$$

where Empty is the signal value of a detector with no fluid in the read area.

6. The method of claim 1 further comprising classifying selected calculations as bubbles, and invalidating the presence of the target substance at times when the bubbles exceed a predetermined value.

* * * * *